United States Patent [19]

Fouché et al.

[11] 4,172,096

[45] Oct. 23, 1979

[54] PROCESS FOR THE PREPARATION OF ASYMMETRIC DIMETHYLHYDRAZINE IN THE PRESENCE OF HYDRAZINE

[75] Inventors: Serge Fouché, Vernon; Michel Lemaitre, Forêt de Vernon, both of France

[73] Assignee: Societe Europeenne de Propulsion, Puteaux, France

[21] Appl. No.: 953,183

[22] Filed: Oct. 20, 1978

[30] Foreign Application Priority Data

Oct. 24, 1977 [FR] France .................................. 77 31971

[51] Int. Cl.$^2$ ............................................. C07C 109/02
[52] U.S. Cl. ............................. 260/583 B; 260/583 N
[58] Field of Search ...................................... 260/583 B

[56] References Cited

U.S. PATENT DOCUMENTS

| | | | |
|---|---|---|---|
| 2,806,851 | 9/1957 | Sisler et al. ................... | 260/583 B X |
| 2,808,439 | 10/1957 | Barrett et al. ................... | 260/583 B |
| 2,876,173 | 3/1959 | Nicolaisen .................... | 260/583 B X |
| 3,015,675 | 1/1962 | Hurley ............................ | 260/583 B |
| 3,050,560 | 8/1962 | Randolph et al. ............... | 260/583 B |
| 3,168,568 | 2/1965 | Clark et al. ..................... | 260/583 B |
| 3,254,952 | 6/1966 | Raleigh et al. ................. | 260/583 B X |
| 3,305,585 | 2/1967 | Besson et al. .................... | 260/583 B |

FOREIGN PATENT DOCUMENTS

| | | | |
|---|---|---|---|
| 582143 | 8/1959 | Belgium ............................ | 260/583 B |
| 624393 | 7/1961 | Canada .............................. | 260/583 B |
| 1274393 | 9/1961 | France ............................... | 260/583 B |
| 39-15661 | 8/1964 | Japan ................................. | 260/583 B |

*Primary Examiner*—Winston A. Douglas
*Assistant Examiner*—John Doll
*Attorney, Agent, or Firm*—Lewis H. Eslinger

[57] ABSTRACT

The present invention relates to a process for the preparation of asymmetric dimethylhydrazine by a reaction capable of producing, as impurity, formaldehyde dimethylhydrazone, wherein said reaction is effected in the presence of hydrazine.

4 Claims, No Drawings

PROCESS FOR THE PREPARATION OF ASYMMETRIC DIMETHYLHYDRAZINE IN THE PRESENCE OF HYDRAZINE

The present invention relates to an improved process for the preparation of asymmetric dimethylhydrazine.

The synthesis of the asymmetric dimethylhydrazine (ADMH) is effected at the present time in the following two stages:

$$NH_3 + NaOCl \xrightarrow{(Cl.NH_4)} NH_2Cl + NaOH \quad (1)$$

$$NH_2Cl + (CH_3)_2NH + NaOH \rightarrow (CH_3)_2N-NH_2 + NaCl + H_2O \quad (2)$$

These two reactions are effected successively in two different reactors which are connected together so as to take into account the limited life duration of the chloramine.

The second reaction is effected by sending into an aqueous solution containing an excess of dimethylamine and sodium hydroxide, a cold solution containing—according to the operating conditions employed in the first reaction—about 0.2 to 2 mols/liter of chloramine.

During this second reaction, a certain quantity of impurities, particularly formaldehyde dimethylhydrazone (FDMH): $(CH_3)_2N-N=CH_2$, is formed at the same time as the desired ADMH.

The present invention relates to a means, all else being equal, for reducing the quantity of FDMH formed during the second reaction, namely the reaction, in an aqueous medium, of the chloramine on the dimethylamine (DMA) in the presence of sodium hydroxide; this means consists in effecting said reaction in the presence of hydrazine.

The hydrazine used according to the present invention must preferably be introduced with the reagents of the second reaction and, more generally, during the ADMH forming reaction, so that its effect is felt during the whole of the reaction and this is not limiting. When this second reaction is effected continuously, it will essentially be envisaged to maintain a certain concentration of hydrazine in the reactional medium.

The quantities of hydrazine introduced in the discontinuous reactions are included between about 0.5 and 2% by volume with respect to the volume of the solution of chloramine used.

In practice, particularly for continuous reactions, the quantities of hydrazine to be used will be adapted as a function of the quantities of FDMH produced during the reactions effected, all else being equal, in the absence of hydrazine. Thus, to determine the quantities of hydrazine to be used, the reaction will be carried out in the absence of hydrazine and, at equilibrium, the concentration of the FDMH will be determined in the reactional medium. A quantity of hydrazine will then be used such that its concentration in the medium will be about 3 to 20 times the concentration in FDMH expressed in mols per liter.

In all cases (discontinuous or continuous reaction), the hydrazine may be used either in pure form or in the form of hydrate (i.e. in aqueous solution).

With present knowledge, it may be thought that the mode of action of the hydrazine in the process according to the invention consists in a reaction of the hydrazine on the FDMH according to the following equation:

$$NH_2-NH_2 + (CH_3)_2-N-N=CH_2 \rightarrow CH_2=N-NH_2 + (CH_3)_2-N-NH_2.$$

It may therefore be thought that in all the reactions which may be used for effecting the synthesis of asymmetric dimethylhydrazine in which FDMH will appear, the presence of hydrazine will inhibit or limit the concentration of FDMH in the reactional medium.

The following non-limiting examples illustrate the invention.

EXAMPLE 1

In a first reactor whose temperature is regulated by a circulation of methanol at −10° C. and provided with a magnetic stirrer, are introduced 75 ml of a $NH_3$—$NH_4Cl$ solution containing for 500 ml:

250 ml of an aqueous solution of ammonia (19.6% by weight):

250 ml water 80 grams of $NH_4Cl$

After thermic equilibrium, 100 ml of a solution of sodium hypochlorite titrating 1.52 M/l are added drop by drop so that the temperature never exceeds 0° C.

In a first three-necked, 250 ml flask (test A), provided with a magnetic stirrer and previously placed under an inert nitrogen atmosphere, there are introducted:

30 ml of an aqueous solution of dimethylamine (35.7% by weight) (d=0.91)

10 ml of a sodium hydroxide solution with 480 g/liter, or: 12 M/l.

A separation of the constituents is then observed, hence the necessity of a vigourous stirring in order to emulsify the two phases.

50 ml of the aqueous solution of chloramine prepared previously and maintained cold, are then introduced rapidly. The temperature rises to 30° C. then is stabilised at about 20° C.

In a second three-necked, 250 ml flask (test B), there are introduced:

30 ml of the preceding aqueous solution of dimethylamine, 10 ml of the preceding sodium hydroxide solution, then is added 0.25 ml of anhydrous hydrazine, then finally 50 ml of the solution of chloramine.

The reactional liquids of the two reactors are then analysed by gas phase chromatography respectively after 2 hours, 15 minutes of reaction; the results are grouped together in Table I hereinafter where the concentrations are expressed in percentages by weight.

TABLE I

|  |  | without $N_2H_4$ (A) | with $N_2H_4$ (B) |
|---|---|---|---|
| [ADMH] | % | 2.50 | 2.50 |
| [FDMH] | % | 0.16 | 0.06 |
| $\dfrac{[FDMH]}{[ADMH]}$ | % | 6.4 | 2.4 |

In the synthesis effected with hydrazine, a reduction of the content of FDMH of 62% with respect to the synthesis effected without hydrazine is therefore observed.

EXAMPLE 2

Two other tests were carried out as in Example 1, using a quantity of hydrazine introduced in the reactor (test B) equal to 0.5 ml with, moreover, the same modus operandi and the same reagents. The results obtained after 4 hours of reaction are shown in Table II hereinafter:

TABLE II

|  |  | without $N_2H_4$ (A) | with $N_2H_4$ (B) |
|---|---|---|---|
| [ADMH] | % | 2.3 | 2.5 |
| [FDMH] | % | 0.31 | 0.09 |
| [FDMH]/[ADMH] | % | 13.5 | 3.6 |

In this example, a reduction in the content of FDMH equal to 71% is observed in reactor B with respect to reactor A.

What is claimed is:

1. A process for the preparation of asymmetric dimethylhydrazine by a reaction capable of producing, as impurity, formaldehyde dimethylhydrazone wherein, said reaction is effected in the presence of hydrazine.

2. The process of claim 1, wherein the asymmetric dimethylhydrazine is prepared by reaction of dimethylamine on chloramine in the presence of sodium hydroxide and this reaction is effected in the presence of hydrazine.

3. The process of claim 2, wherein the quantity of hydrazine used is equal to 0.5 to 2% by volume with respect to the volume of the solution of chloramine used.

4. The process of claim 1, wherein the concentration of hydrazine used, expressed in mols per liter, is equal to about 3 to 20 times the concentration of formaldehyde dimethylhydrazone which would have been formed in the same reaction, carried out, all else being equal, in the absence of hydrazine.

* * * * *